US012605161B2

(12) United States Patent
Wei

(10) Patent No.: US 12,605,161 B2
(45) Date of Patent: Apr. 21, 2026

(54) VISUAL PRESSURE REGULATING CATHETER

(71) Applicant: QINGDAO BIOTECH MEDICAL CO., LTD, Qingdao (CN)

(72) Inventor: Yan Wei, Qingdao (CN)

(73) Assignee: QINGDAO BIOTECH MEDICAL CO., LTD, Qingdao (CN)

( * ) Notice: Subject to any disclaimer, the term of this patent is extended or adjusted under 35 U.S.C. 154(b) by 434 days.

(21) Appl. No.: 18/556,500

(22) PCT Filed: Apr. 19, 2022

(86) PCT No.: PCT/CN2022/087558
§ 371 (c)(1),
(2) Date: Oct. 20, 2023

(87) PCT Pub. No.: WO2022/222903
PCT Pub. Date: Oct. 27, 2022

(65) Prior Publication Data
US 2024/0398418 A1 Dec. 5, 2024

(30) Foreign Application Priority Data
Apr. 20, 2021 (CN) .......................... 202110422876.5

(51) Int. Cl.
*A61B 17/12* (2006.01)
*A61B 1/32* (2006.01)
(Continued)

(52) U.S. Cl.
CPC .......... *A61B 17/12136* (2013.01); *A61B 1/32* (2013.01); *A61M 25/0136* (2013.01);
(Continued)

(58) Field of Classification Search
CPC ................ A61B 17/12136; A61B 1/32; A61B 2017/00539; A61B 1/00082;
(Continued)

(56) References Cited

U.S. PATENT DOCUMENTS 5,007,898 A 4/1991 Rosenbluth et al.
5,259,364 A 11/1993 Bob et al.
(Continued)

FOREIGN PATENT DOCUMENTS

CN 203954435 U 11/2014
CN 104507380 A 4/2015
(Continued)

OTHER PUBLICATIONS

European Search Report issued in counterpart European Patent Application No. EP 22791011.4, dated Aug. 4, 2025.
(Continued)

*Primary Examiner* — Andrew Restaino
(74) *Attorney, Agent, or Firm* — Westbridge IP LLC

(57) ABSTRACT

A visual pressure regulating catheter includes: a catheter body, and a hydraulic dilation balloon and a pressure regulating handle both of which are disposed on the catheter body, an endoscope pressure regulating cavity and a dilation liquid perfusion cavity are formed in the catheter body, the dilation liquid perfusion cavity is communicated with the hydraulic dilation balloon, and the pressure regulating handle is provided with a perfusion port which is communicated with the dilation fluid perfusion cavity and a pressure regulating port which is communicated with the endoscope pressure regulating cavity; an observation channel is opened at a position on the endoscope pressure regulating cavity axially opposite to the hydraulic dilation balloon, a camera at a front end of the endoscope sequentially passes through the pressure regulating port, the endoscope pressure
(Continued)

regulating cavity and the observation channel and extends into the hydraulic dilation balloon.

13 Claims, 10 Drawing Sheets

(51) Int. Cl.
　　*A61B 17/00*　　　(2006.01)
　　*A61M 25/01*　　　(2006.01)
　　*A61M 25/10*　　　(2013.01)
(52) U.S. Cl.
　　CPC ................. *A61M 25/10185* (2013.11); *A61B 2017/00539* (2013.01)
(58) Field of Classification Search
　　CPC . A61B 1/00135; A61B 1/00154; A61B 1/015; A61M 25/0136; A61M 25/10185; A61M 25/104; A61M 25/10184; A61M 29/02; A61M 2025/1052; A61M 2025/1086; A61M 25/10; A61M 25/1018
　　See application file for complete search history.

(56) References Cited

U.S. PATENT DOCUMENTS

| | | | |
|---|---|---|---|
| 8,968,269 B2 | 3/2015 | Becker | |
| 2006/0241345 A1 | 10/2006 | Oishi et al. | |
| 2008/0097292 A1* | 4/2008 | Cabiri | A61B 1/00082 |
| | | | 604/95.01 |
| 2011/0082450 A1 | 4/2011 | Melsky et al. | |
| 2012/0078039 A1 | 3/2012 | Tai et al. | |
| 2017/0215839 A1 | 8/2017 | Pauker | |
| 2017/0291010 A1* | 10/2017 | Bonneau | A61M 25/1011 |
| 2019/0117044 A1* | 4/2019 | Anderson | A61B 1/051 |

FOREIGN PATENT DOCUMENTS

| | | | |
|---|---|---|---|
| CN | 204293125 U | 4/2015 | |
| CN | 105559734 A | 5/2016 | |
| CN | 205460381 U | 8/2016 | |
| CN | 107343980 A | 11/2017 | |
| CN | 107596539 A | 1/2018 | |
| CN | 108159550 A | 6/2018 | |
| CN | 209864988 U | 12/2019 | |
| CN | 111617369 A | 9/2020 | |
| CN | 211383384 U | 9/2020 | |
| CN | 111772876 A | 10/2020 | |
| CN | 212593454 U | 2/2021 | |
| CN | 113244502 A | 8/2021 | |
| CN | 113244503 A | 8/2021 | |
| CN | 216855482 U | 7/2022 | |
| JP | H05501367 A | 3/1993 | |
| JP | 2893833 B | 5/1999 | |
| JP | 2002301019 A | 10/2002 | |
| KR | 101452683 B1 | 10/2014 | |
| WO | 8800844 A1 | 2/1988 | |

OTHER PUBLICATIONS

First Office Action issued in counterpart Chinese Patent Application No. 202110422876.5, dated Oct. 25, 2024.

International Search Report issued in corresponding PCT Application No. PCT/CN2022/087558, dated Jun. 28, 2022.

Search Report made by China Patent Information Center issued in counterpart Chinese Patent Application No. 202110422876.5, dated Jul. 1, 2022.

Supplementary Search Report issued in counterpart Chinese Patent Application No. 202110422876.5, dated Feb. 28, 2025.

* cited by examiner

VISUAL PRESSURE REGULATING CATHETER

CROSS-REFERENCE TO RELATED APPLICATION

The application is a National Stage of International Application No. PCT/CN2022/087558, filed on Apr. 19, 2022, which claims priority to Chinese Patent Application No. 202110422876.5, entitled "visual pressure regulating catheter", and filed on Apr. 20, 2021. All of the aforementioned applications are incorporated herein by reference in their entireties.

TECHNICAL FIELD

The present disclosure relates to the technical field of medical instruments, further to a visual pressure regulating catheter, and particularly to a catheter which is cooperated with an endoscope to accurately adjust a dilation portion and a dilation pressure of a balloon during dilation treatment of an organ tissue orifice and a blood vessel.

BACKGROUND

At present, it is increasingly popular to perform dilation treatment for various diseases by introducing a balloon catheter into a blood vessel or other tissue lumen of a patient (e.g., a lesion site such as vagina, urinary tract, airway, intestine, biliary tract or esophagus). The basic principle of the application of the balloon catheter is that a mechanical dilation pressure is transmitted to a lesion site by dilating a balloon to treat the lesion site. After the balloon catheter is completely dilated, air is sucked from the balloon for pressure reduction. While the balloon after pressure reduction decreases the mechanical pressure to a lesion tissue, an outer diameter of the balloon is also greatly reduced due to the pressure reduction. The conventional clinical dilatation treatment mainly lies on auxiliary devices for angiography, B-scan ultrasonography, etc. to determine a dilatation part and a dilatation pressure in a surgical procedure. Since the image from the auxiliary device is not an intuitive image, the operation process is greatly influenced by the operator's experience.

In the prior art, the use of endoscope for medical diagnosis has been widely used in the medical field. The endoscope is an important means of diagnosis, which enters a natural orifice of a human body and provide intuitive images to inspect the internal structure of the orifice. Through the matched surgical instrument, it is also possible to finely treat the orifice, so that the surgical procedure is safer and more effective. Therefore, the dilation treatment for the lesion site in the orifice using a balloon catheter assisted with an endoscope is more and more widely used in clinical practices, such as in the esophagus, intestinal tract or urinary tract. A dilatation surgical operation using a balloon catheter assisted with an endoscope mainly has two operation modes: one is to deliver a surgical instrument to the lesion site by means of an endoscopic instrument cavity, and the other is to push the endoscope and surgical instrument to the lesion site in parallel. Since the balloon catheter and the endoscope are independent from each other, the above two modes have the following defects:

1. when a narrow orifice is treated during operation, the balloon catheter and endoscope interact with each other due to an extrusion from the orifice, the operation is inconvenient, and it is often impossible to observe the condition of the instrument at all, and the operation is substantially completely blind or semi-blind;

2. the balloon catheter and endoscope are in front and rear positions, and the positioning and dilation process of the balloon cannot be accurately observed by the endoscope, so it is impossible to adjust the dilation site and the dilation pressure in real time, which brings great inconvenience to the operation.

At present, there is no effective solution to the problem of the inconvenience and poor use effect of the balloon catheter in cooperation with the endoscope in the related art.

SUMMARY

An objective of the present disclosure is to provide a visual pressure regulating catheter, which is simple and convenient to operate, greatly improves the positioning efficiency of an endoscope by guidance, cooperates with the endoscope to adjust the positioning and dilation of a balloon, and allows a lesion site being dilated to be observed in real time by the endoscope in a dilation process of the balloon, so as to prevent a dilation treatment from being failed due to sliding of the balloon in the dilation process.

Another objective of the present disclosure is to provide a visual pressure regulating catheter, which allows tissue changes in a dilation process to be observed in real time by an endoscope, and accurately adjusts an inflation pressure of a balloon by adjusting the position of the endoscope in a pressure regulating cavity, thereby greatly improving the surgery efficiency and effect.

Still another objective of the present disclosure is to provide a visual pressure regulating catheter, which provides a local linear pressure to a lesion site in a state where a balloon is fully dilated, and segment a severely hyperplastic stenotic lesion tissue into a plurality of lesion areas to reduce the resilience of the lesion site after dilation, thereby improving the surgical treatment effect.

The objectives of the present disclosure may be achieved by the following technical solutions.

The present disclosure provides a visual pressure regulating catheter, including: a catheter body, and a hydraulic dilation balloon and a pressure regulating handle both of which are disposed on the catheter body, an endoscope pressure regulating cavity and a dilation liquid perfusion cavity are formed in the catheter body along an extension direction thereof, the dilation liquid perfusion cavity is communicated with the hydraulic dilation balloon, and the pressure regulating handle is provided with a perfusion port which is communicated with the dilation fluid perfusion cavity and a pressure regulating port which is communicated with the endoscope pressure regulating cavity:

an observation channel is opened at a position on the endoscope pressure regulating cavity axially opposite to the hydraulic dilation balloon, a camera at a front end of the endoscope sequentially passes through the pressure regulating port, the endoscope pressure regulating cavity and the observation channel and extends into the hydraulic dilation balloon, and an operating rod at a tail end of the endoscope is slidably and sealingly connected to the pressure regulating port.

The present disclosure has the following advantageous effects:

1. The visual pressure regulating catheter is provided therein with the dilation liquid perfusion cavity and the endoscope pressure regulating cavity. The endoscope is used in cooperation with the hydraulic dilation balloon, and synchronously observes the situation in the cavity in real time in a process of delivering liquid into the hydraulic dilation balloon and positioning the hydraulic dilation balloon, thereby reducing the operation difficulty caused by the independent positions of the endoscope and the balloon catheter in the prior art, and improving the efficiency and effect of catheter delivery and positioning.

2. In the visual pressure regulating catheter, the operating rod at the tail end of the endoscope is slidably and sealingly connected to the pressure regulating port, and the endoscope may observe and confirm the action position of the hydraulic dilation balloon in real time when the hydraulic dilation balloon is performed to a dilation treatment of the lesion site, so as to prevent the dilation treatment from being failed due to sliding of the hydraulic dilation balloon. In addition, the volume of the endoscope entering the catheter body and the position of the endoscope are adjusted by pushing in or pulling out the operating rod of the endoscope, so as to adjust the pressure in the closed chamber, thereby accurately adjusting the dilation pressure of the hydraulic dilation balloon in real time, and avoiding a poor treatment effect due to insufficient or excessive dilation of the hydraulic dilation balloon.

3. The visual pressure regulating catheter is used in cooperation with various conventional clinical instruments based on the needs of the clinical treatment, and the operation is convenient, thereby avoiding complications caused by a cavity injury due to instrument changing, and effectively improving the clinical treatment effect.

4. In the visual pressure regulating catheter, by disposing the local pressure reinforcing rib outside the hydraulic dilation balloon, it is possible to provide a local linear pressure to the lesion site under the condition that the hydraulic dilation balloon is fully dilated and expanded, and dilate the lesion site and segment it into a plurality of areas for treatment without greatly increasing the dilation pressure of the hydraulic dilation balloon, thereby greatly reducing the resilience of the lesion tissue after the dilation treatment, especially achieving a very excellent treatment effect on a severely hyperplastic stenotic lesion tissue for which the effect of a simple balloon dilation treatment is poor.

BRIEF DESCRIPTION OF THE DRAWINGS

The following drawings are only intended to schematically illustrate and explain the present disclosure, rather than limiting the scope thereof. In the drawings.

DETAILED DESCRIPTION OF THE EMBODIMENTS

Figure 1:
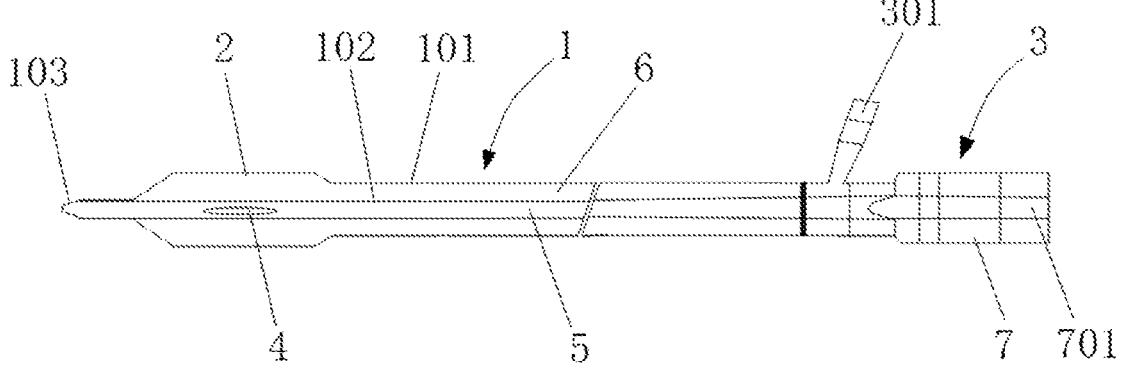
FIG. 1 illustrates a structural diagram of a visual pressure regulating catheter of the present disclosure.

In order to have a clearer understanding of the technical features, objectives and effects of the present disclosure, specific embodiments of the present disclosure will now be described with reference to the drawings.

As illustrated in FIGS. 1 to 16, the present disclosure provides a visual pressure regulating catheter, and the visual pressure regulating catheter includes a catheter body 1, and a hydraulic dilation balloon 2 and a pressure regulating handle 3 both of which are disposed on the catheter body 1; an endoscope pressure regulating cavity 5 and a dilation liquid perfusion cavity 6 are formed in the catheter body 1 along an extension direction thereof, and the dilation liquid perfusion cavity 6 is communicated with an interior of the hydraulic dilation balloon 2; the pressure regulating handle 3 is provided with a perfusion port 301 and a pressure regulating valve 7, the pressure regulating valve 7 is provided with a pressure regulating port 701, the perfusion port 301 is communicated with the dilation fluid perfusion cavity 6, and the pressure regulating port 701 is communicated with the endoscope pressure regulating cavity 5; an observation channel 4 is opened at a position on the endoscope pressure regulating cavity 5 axially opposite to the hydraulic dilation balloon 2; a camera at a front end of the endoscope sequentially passes through the pressure regulating port 701, the endoscope pressure regulating cavity 5 and the observation channel 4, and extends into the hydraulic dilation balloon 2; an operating rod at a tail end of the endoscope is slidably and sealingly connected to the pressure regulating port 701, so that a closed chamber with a fixed volume is formed inside the endoscope pressure regulating cavity 5, the dilation liquid perfusion cavity 6 and the hydraulic dilation balloon 2; and the part of the endoscope located in the closed chamber is controlled to move by pulling out or pushing in the operating rod of the endoscope outside the pressure regulating port 701, so as to change a space proportion of the endoscope in the closed chamber, thereby flexibly and accurately adjusting a dilation pressure of the hydraulic dilation balloon 2.

During the application of the present disclosure, liquid is delivered into the dilation liquid perfusion cavity 6 through the perfusion port 301, so as to control the dilation of the hydraulic dilation balloon 2 and achieve the purpose of treating the lesion site. In addition, the pressure regulating port 701 is configured as an insertion port of the endoscope, and the camera at the front end of the endoscope sequentially passes through the pressure regulating port 701, the endoscope pressure regulating cavity 5 and the observation channel 4, and extends into the hydraulic dilation balloon 2. In this process, the endoscope not only observes the situation in the cavity in real time, but also observes and confirms the position of the hydraulic dilation balloon 2 in real time throughout the dilation treatment process by the hydraulic dilation balloon 2, so as to prevent the failure of the dilation treatment caused by the sliding of the hydraulic dilation balloon 2 and ensure the smooth progression of the dilation treatment. Since the operating rod at the tail end of the endoscope is slidably and sealingly connected to the pressure regulating port 701, a closed chamber is formed inside the catheter body 1. During use, the pressure in the closed chamber is adjusted by adjusting the volume of the endoscope entering the catheter body 1 and the position of the endoscope, so as to accurately adjust the dilation pressure of the hydraulic dilation balloon 2. In this process, there is no need to perfuse liquid into or extract liquid from the hydraulic dilation balloon 2 by the dilation liquid injection cavity 6, which avoids the problem of poor treatment effect caused by insufficient or excessive dilation of the hydraulic dilation balloon 2, thereby improving the treatment effect on the lesion site.

Further, the perfusion port 301 may be configured with, but is not limited to, a Luer taper.

Further, a length of the catheter body 1 is 10 cm to 250 cm, and an outer diameter of the catheter body 1 is 0.1 cm to 1.5 cm.

Further, when the hydraulic dilation balloon 2 is in a fully dilated state, an axial length (i.e., an effective working section length of the hydraulic dilation balloon 2) of the area where the hydraulic dilation balloon 2 contacts the lesion site is 1 mm to 300 mm, and a diameter (effective dilation diameter) of the hydraulic dilation balloon 2 is 1 mm to 100 mm.

Further, an axial length of the observation channel 4 in the endoscope pressure regulating cavity 5 is 3 mm to 50 mm.

In an alternative embodiment of the present disclosure, as illustrated in FIG. 1, the catheter body 1 includes the pressure regulating handle 3 disposed at one end thereof, and a tapered sealing head 103 disposed at the other end thereof, and the hydraulic dilation balloon 2 is disposed to be close to the sealing head 103 through which a guiding function is realized, so as to facilitate the delivery of the hydraulic dilation balloon 2 to a lesion site of a patient.

Further, both the catheter body 1 and the sealing head 103 are made of plastic materials. optional, both the catheter body 1 and the sealing head 103 are made of transparent plastic materials.

Figure 2:
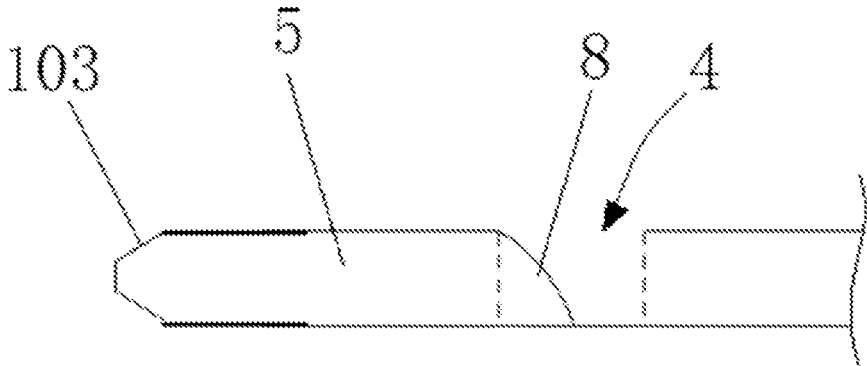
FIG. 2 illustrates a structural diagram of a steering guide piece of a visual pressure regulating catheter of the present disclosure.

In an alternative embodiment of the present disclosure, as illustrated in FIG. 2, a side of the observation channel 4 away from the pressure regulating handle 3 is provided with a steering guide piece 8, and the steering guide piece 8 is provided with an arc-shaped edge inclined to the outside of the endoscope pressure regulating cavity 5. When the endoscope is delivered to the observation channel 4 by the endoscope pressure regulating cavity 5, the steering guide piece 8 guides the endoscope by means of the arc-shaped edge, thereby assisting the endoscope to steer and extending into the interior of the hydraulic dilation balloon 2.

Figure 3:
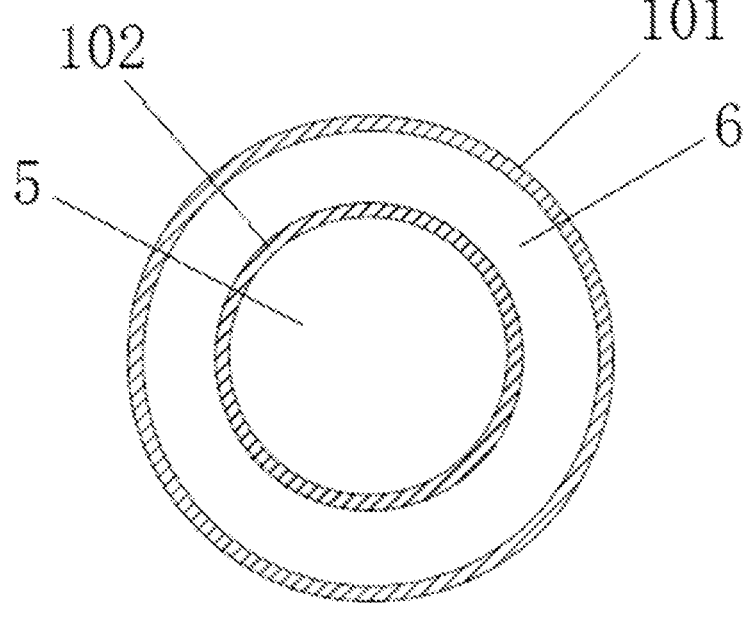
FIG. 3 illustrates a first cross-sectional view of a catheter body in an embodiment of a visual pressure regulating catheter of the present disclosure.
Figure 4:
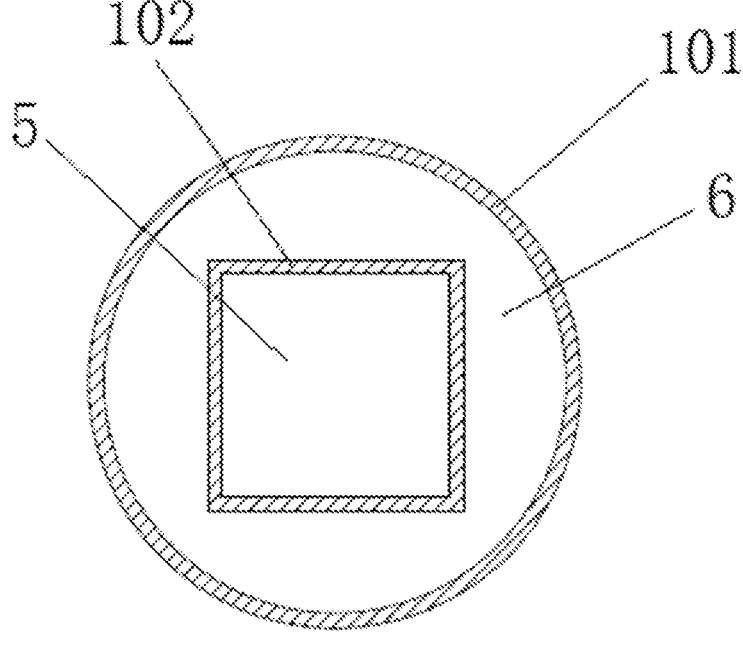
FIG. 4 illustrates a second cross-sectional view of a catheter body in an embodiment of a visual pressure regulating catheter of the present disclosure.

In an alternative embodiment of the present disclosure, as illustrated in FIGS. 3 and 4, the endoscope pressure regulating cavity 5 and the dilation liquid perfusion cavity 6 are coaxially disposed (i.e., the interior of the catheter body 1 is a coaxial double-cavity structure), and the dilation liquid perfusion cavity 6 is annularly disposed outside the endoscope pressure regulating cavity 5. The cross-section of the endoscope pressure regulating cavity 5 is a circular or square shape, and the cross-section of the dilation liquid perfusion cavity 6 is an annular or crescent shape.

Specifically, as illustrated in FIGS. 1, 3 and 4, the catheter body 1 includes an inner catheter body 102 and an outer catheter body 101 disposed to sleeve the outside of the inner catheter body 102, so as to form the endoscope pressure regulating cavity 5 in the inner catheter body 102, and form the dilation liquid perfusion cavity 6 between the inner catheter body 102 and the outer catheter body 101. An end of the hydraulic dilation balloon 2 away from the pressure regulating handle 3 is integrally connected to the inner catheter body 102, and an end of the hydraulic dilation balloon 2 close to the pressure regulating handle 3 is connected to the outer catheter body 101. The observation channel 4 sequentially passes through the inner catheter body 102 and the outer catheter body 101 and is communicated with the interior of the hydraulic dilation balloon 2. In addition, the inner catheter body 102 may be configured as a reinforcing rib of the outer catheter body 101, so as to enhance the anti-bending capability and the pushing operation performance of the catheter body 1 by the disposition of the inner tube body 102.

Further, the diameter of the inner catheter body 102 is gradually reduced from an end close to the pressure regulating handle 3 to an end away from the pressure regulating handle 3, so that a larger retraction space is provided to the hydraulic dilation balloon 2 when being retracted and folded, and the hydraulic dilation balloon 2 has a smaller radial size after being folded, which is beneficial for the hydraulic dilation balloon 2 to pass through a narrow lesion site.

Figure 5:
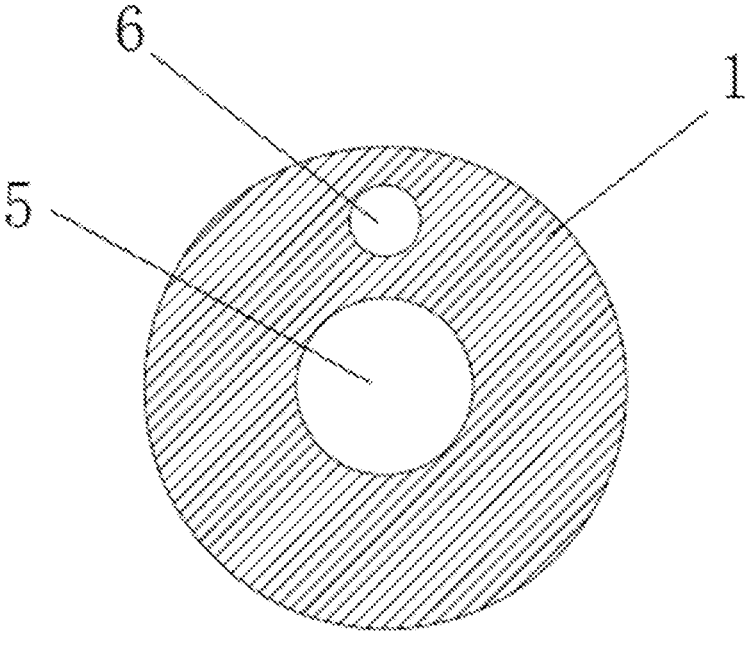
FIG. 5 illustrates a first cross-sectional view of a catheter body in another embodiment of a visual pressure regulating catheter of the present disclosure.
Figure 6:
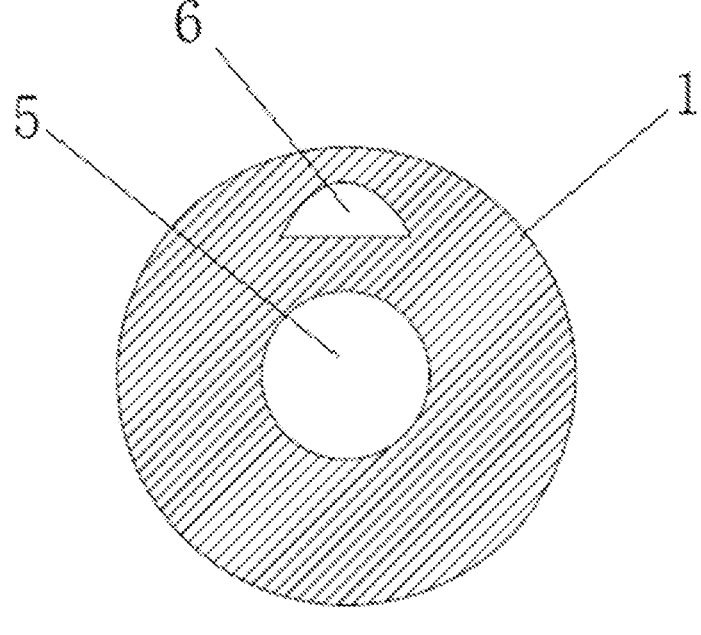
FIG. 6 illustrates a second cross-sectional view of a catheter body in another embodiment of a visual pressure regulating catheter of the present disclosure.

In an alternative embodiment of the present disclosure, as illustrated in FIGS. 5 and 6, a central axis of the endoscope pressure regulating cavity 5 is disposed in parallel with a central axis of the dilation liquid perfusion cavity 6 (i.e., the interior of the catheter body 1 is a non-coaxial double-cavity structure), the endoscope pressure regulating cavity 5 is located at an axial center of the catheter body 1, a cross-sectional area of the endoscope pressure regulating cavity 5 is larger than that of the dilation liquid perfusion cavity 6, both ends of the hydraulic dilation balloon 2 are connected to the catheter body 1, and the observation channel 4 passes through the catheter body 1 and is communicated with the interior of the hydraulic dilation balloon 2. The cross-section of the endoscope pressure regulating cavity 5 is a circular shape, and the cross-section of the dilation liquid perfusion cavity 6 is a circular or crescent shape.

In an alternative embodiment of the present disclosure, the endoscope pressure regulating cavity 5 and the dilation liquid perfusion cavity 6 may be the same common cavity (i.e., the interior of the catheter body 1 is a single cavity structure), and the cross-section of the common cavity is a circular, rhombic or square shape.

Figure 9:
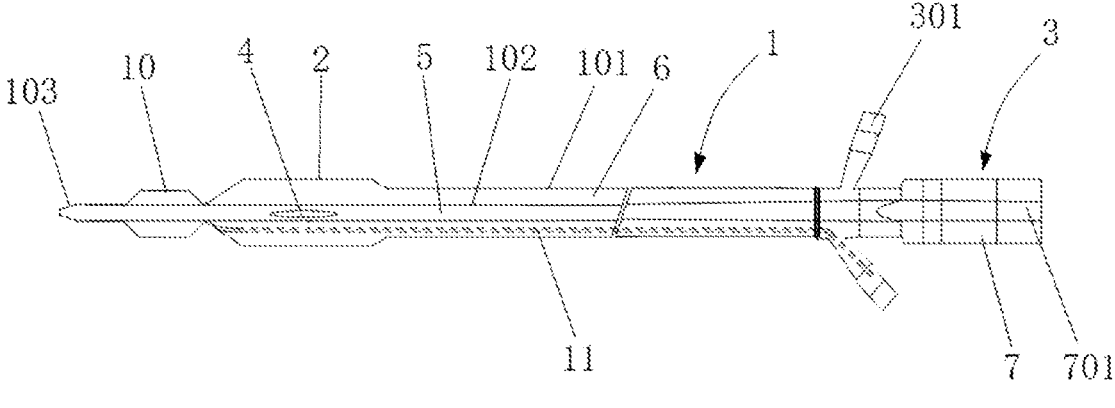
FIG. 9 illustrates a schematic diagram of disposition positions of an occlusion balloon and a dilation liquid perfusion tube in a visual pressure regulating catheter of the present disclosure.
Figure 10:
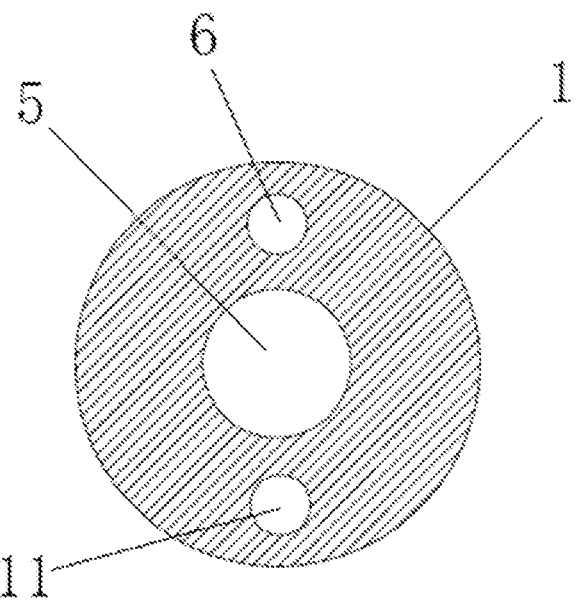
FIG. 10 illustrates a first cross-sectional view of a disposition position of a dilation liquid perfusion tube in a visual pressure regulating catheter of the present disclosure.
Figure 11:
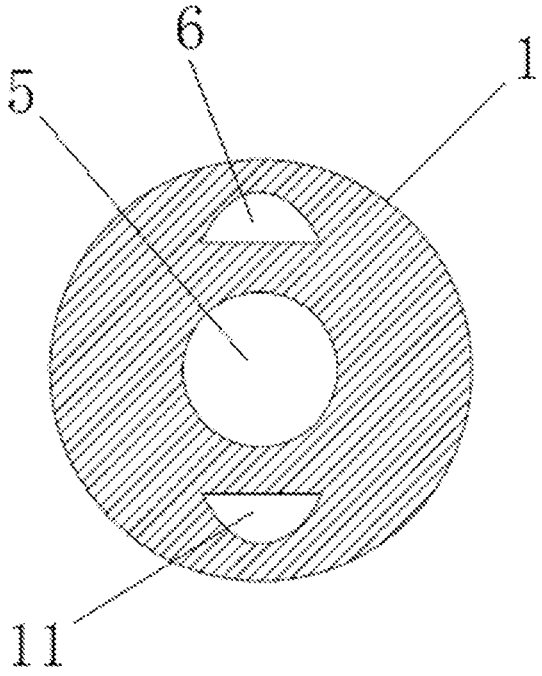
FIG. 11 illustrates a second cross-sectional view of a disposition position of a dilation liquid perfusion tube in a visual pressure regulating catheter of the present disclosure.

In an alternative embodiment of the present disclosure, as illustrated in FIG. 9, an occlusion balloon 10 is disposed at a position on the catheter body 1 close to the hydraulic dilation balloon 2, and a dilation liquid perfusion tube 11 is disposed inside the catheter body 1 and communicated with the interior of the occlusion balloon 10. Liquid is perfused into the occlusion balloon 10 by the dilation liquid perfusion tube 11 to dilate the occlusion balloon 10. In a dilated state, the occlusion balloon 10 is configured to interrupt polluted body fluid from both sides of the hydraulic dilation balloon 2 in the lesion cavity while the dilation treatment is performed, so that the hydraulic dilation balloon 2 achieves a better treatment effect. The occlusion balloon 10 may be located on a left or right side of the hydraulic dilation balloon 2, which is adjusted based on the needs of clinical treatment. If the catheter body 1 is a coaxial double-cavity structure, the dilation liquid perfusion tube 11 is disposed in the dilation liquid perfusion cavity 6 and passes through the dilation liquid perfusion cavity 6 to communicate with the interior of the occlusion balloon 10. If the catheter body 1 is a non-coaxial double-cavity structure, as illustrated in FIGS. 5 and 6, the dilation liquid perfusion tube 11 is disposed in the catheter body 1, and the dilation liquid perfusion tube 11 and the dilation liquid perfusion cavity 6 are symmetrically disposed on two sides of the endoscope pressure regulating cavity 5, in which the size and shape of the cross-section of the dilation liquid perfusion tube 11 are the same as those of the cross-section of the dilation liquid perfusion cavity 6.

Further, the cross-sectional of the dilation liquid perfusion tube 11 may be, but not limited to, a circular shape or a crescent shape.

Figure 7:
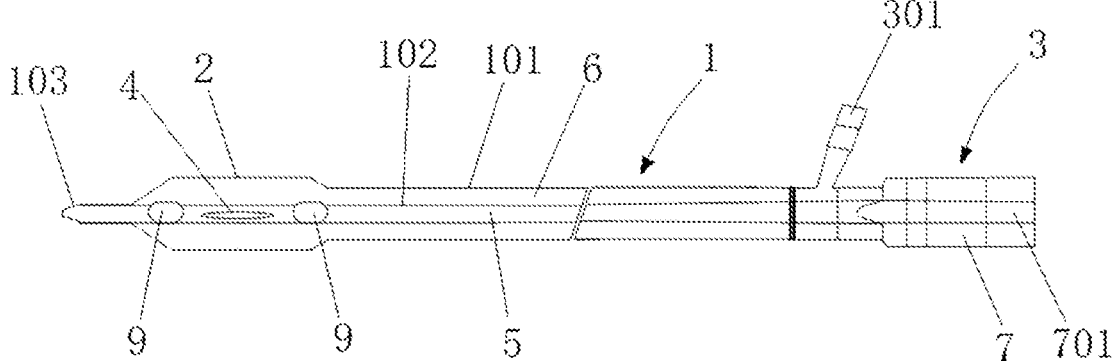
FIG. 7 illustrates a schematic diagram of a mounting position of a developing ring in a visual pressure regulating catheter of the present disclosure.

In an alternative embodiment of the present disclosure, as illustrated in FIG. 7, at least one developing ring 9 is disposed at a position on the catheter body 1 axially opposite to the hydraulic dilation balloon 2. The developing ring 9 may increase the developability of the visual pressure regulating catheter of the present disclosure under X-rays, and improve the positioning performance thereof. If the catheter body 1 is a coaxial double-cavity structure, the developing ring 9 is disposed inside the hydraulic dilation balloon 2 and located on an outer surface of the inner catheter body 102. If the catheter body 1 is a non-coaxial double-cavity structure, the developing ring 9 is disposed inside the hydraulic dilation balloon 2 and located on an outer surface of the catheter body 1.

Specifically, there are two developing rings 9 located on two sides of the hydraulic dilation balloon 2.

Figure 8:
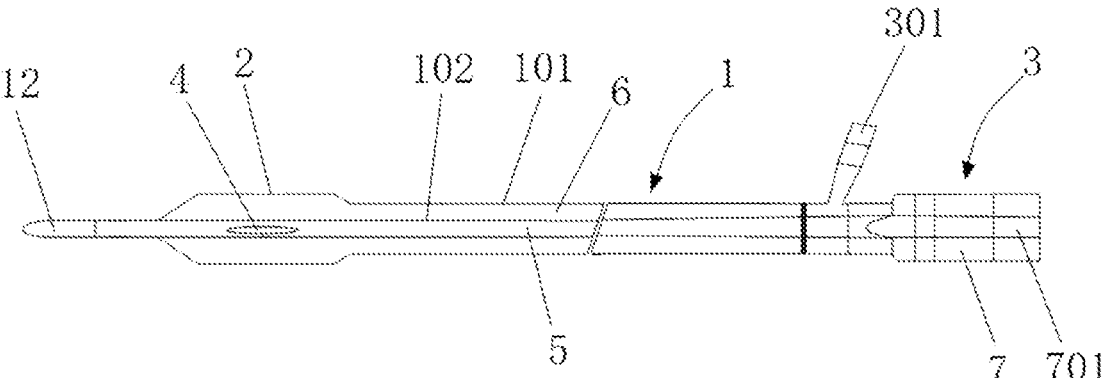
FIG. 8 illustrates a schematic diagram of a mounting position of a guide tube in a visual pressure regulating catheter of the present disclosure.

In an alternative embodiment of the present disclosure, as illustrated in FIG. 8, a guide tube 12 is disposed at an end of the catheter body 1 away from the pressure regulating handle 3, and one end of the guide tube 12 is sealed, and the other end thereof is integrally connected to the catheter body 1. The guide tube 12 achieves a guiding function (similar to the function of a guide wire), which is beneficial for the catheter to pass through a narrow area without being guided by a guide wire during delivery.

Figure 12:
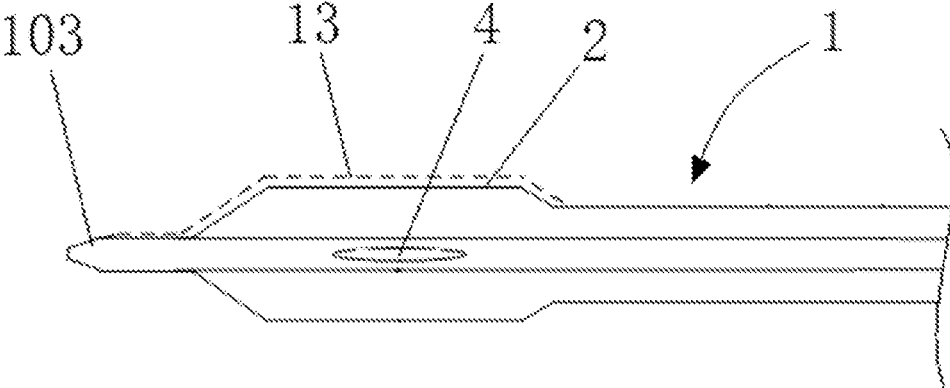
FIG. 12 illustrates a schematic diagram of a disposition position of a local pressure reinforcing rib in a visual pressure regulating catheter of the present disclosure.
Figure 13:
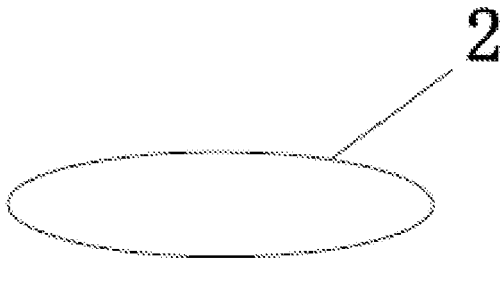
FIG. 13 illustrates a structural diagram of a hydraulic dilation balloon in a first embodiment of a visual pressure regulating catheter of the present disclosure.
Figure 14:
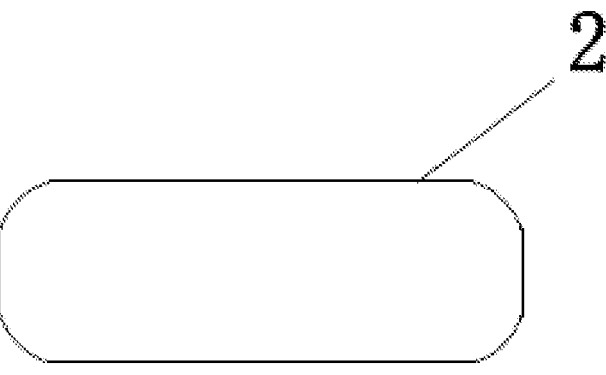
FIG. 14 illustrates a structural diagram of a hydraulic dilation balloon in a second embodiment of a visual pressure regulating catheter of the present disclosure.
Figure 15:
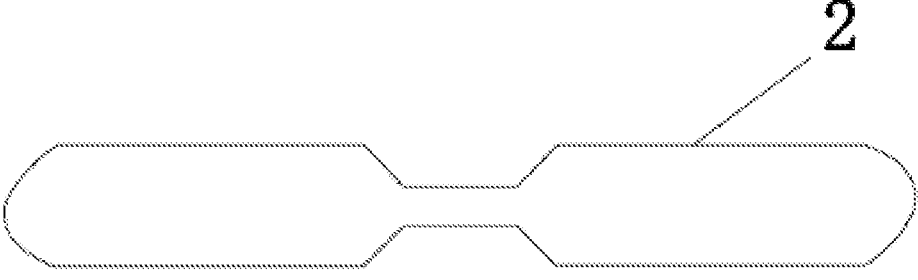
FIG. 15 illustrates a structural diagram of a hydraulic dilation balloon in a third embodiment of a visual pressure regulating catheter of the present disclosure.
Figure 16:
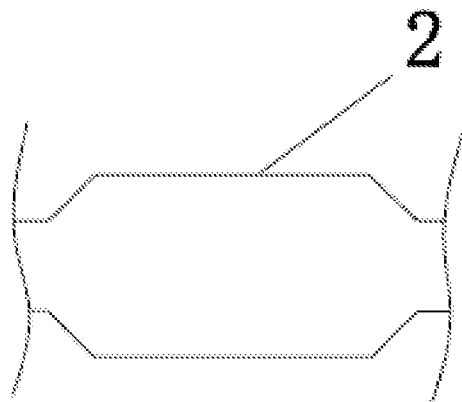
FIG. 16 illustrates a structural diagram of a hydraulic dilation balloon in a fourth embodiment of a visual pressure regulating catheter of the present disclosure.
Figure 17:
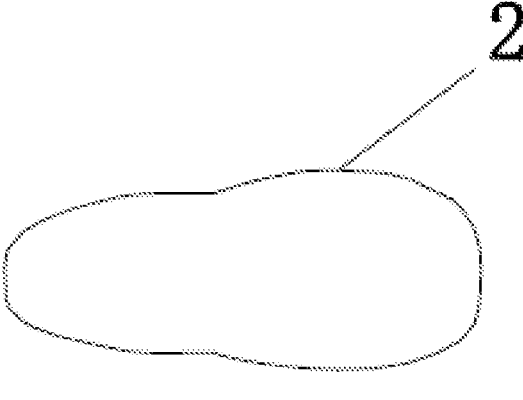
FIG. 17 illustrates a structural diagram of a hydraulic dilation balloon in a fifth embodiment of a visual pressure regulating catheter of the present disclosure.

In an alternative embodiment of the present disclosure, as illustrated in FIG. 12, the hydraulic dilation balloon 2 is externally provided with a local pressure reinforcing rib 13, and one end of the local pressure reinforcing rib 13 is in sealed connection with the catheter body 1, and the other end of the local pressure reinforcing rib 13 extends away from the pressure regulating handle 3 to the end of the catheter body 1 and is in sealed connection with the catheter body 1. In this embodiment, the local pressure reinforcing rib 13 may also be integrally connected to the catheter body 1. Of course, the local pressure reinforcing rib 13 may also be extended to the pressure regulating handle 3 and integrally connected to the catheter body 1 or the pressure regulating handle 3, so as to ensure that the local pressure reinforcing rib 13 covers an outer surface of the hydraulic dilation balloon 2 in an axial direction thereof. By disposing the local pressure reinforcing rib 13, it is possible to provide a local linear pressure to the lesion site under the condition that the hydraulic dilation balloon 2 is fully dilated and expanded, and dilate the lesion site and segment it into a plurality of areas for treatment without greatly increasing the dilation pressure of the hydraulic dilation balloon 2, thereby greatly reducing the resilience of the lesion tissue (e.g., a severely hyperplastic stenotic lesion tissue with a high density and a large resilience) after the dilation treatment, especially achieving a very excellent treatment effect on a severely hyperplastic stenotic lesion tissue for which the effect of a simple balloon dilation treatment is poor. In addition, during the application of the visual pressure regulating catheter of the present disclosure, the segmentation of the lesion tissue may be observed by the endoscope, and when the pressure needs to be increased finely, it is possible to accurately regulate the dilation pressure of the hydraulic dilation balloon 2 by the pressure regulating valve 7 without increasing the liquid in the hydraulic dilation balloon 2, thereby improving the treatment effect.

Further, the number of the local pressure reinforcing rib 13 may be, but not limited to, 1 to 7. An extension direction of each of the local pressure reinforcing ribs 13 is parallel to an axial direction of the hydraulic dilation balloon 2 (i.e., an action direction of the hydraulic dilation balloon 2 during working), and the local pressure reinforcing ribs 13 are distributed on the outer surface of the hydraulic dilation balloon 2 along a circumferential direction thereof. The cross-section of the local pressure reinforcing rib 13 is an arc-shaped, triangular, rhombic or square structure. The height of the local pressure reinforcing rib 13 (i.e., a contact distance between the local pressure reinforcing rib 13 and the lesion site) may be adjusted depending on the actual lesion site, so that the outer surface of the local pressure reinforcing rib 13 can segment the lesion site into a plurality of areas for treatment. When the cross-section of the local pressure reinforcing rib 13 is a triangular, rhombic or square shape, a sharp outer edge of the local pressure reinforcing rib 13 (the sharp outer edge is only located at a position where the local pressure reinforcing rib 13 is axially opposite to the hydraulic dilation balloon 2, or only at a part of that position) segments the lesion site.

Further, the local pressure reinforcing rib 13 may be made of, but not limited to, metal or hard plastic.

In an alternative embodiment of the present disclosure, there may be one hydraulic dilation balloon 2 or a plurality of hydraulic dilation balloons 2 disposed continuously along an axial direction of the catheter body 1, and the hydraulic dilation balloon 2 is made of a transparent material.

Further, the hydraulic dilation balloon 2 may be made of a single-layer material, which is selected from any of polyvinyl chloride, polyurethane, nylon or polyether block amide: and the hydraulic dilation balloon 2 may be made of multilayer materials, and each of multilayer materials may be selected from any of polyvinyl chloride, polyurethane, nylon or polyether block amide.

Further, as illustrated in FIGS. 13 to 17, the shape of the hydraulic dilation balloon 2 may be, but not limited to, elliptical or cylindrical. Of course, the hydraulic dilation balloon 2 may also be a special-shaped columnar structure (e.g., a dumbbell structure with a large diameter at either end and a small diameter in the middle; a tapered structure with a large diameter in the middle and a gradually reduced diameter toward either end; or a wedge structure with a large diameter at one end and a small diameter at the other end).

Since the visual pressure regulating catheter of the present disclosure is provided with the endoscope pressure regulating cavity 5, other instruments may be disposed in the catheter by the endoscope pressure regulating cavity 5 to cooperate with the hydraulic dilation balloon 2. Optionally, other instruments include an ultrasonic probe, a radiotherapy catheter, a laser device, etc.

The working process of the present disclosure is as follows: an external balloon dilation pump is connected to the perfusion port 301 on the pressure regulating handle 3, and the purpose of perfusing liquid into the hydraulic dilation balloon 2 to expand and dilate the hydraulic dilation balloon 2 is achieved by passing through the perfusion port 301 and the dilation liquid injection cavity 6 in turn. Since the pressure regulating port 701 is also an insertion port of the endoscope, during operation, the endoscope is inserted from the pressure regulating port 701, and reaches a preset position in the hydraulic dilation balloon 2 passing through the endoscope pressure regulating cavity 5 and the observation channel 4 in turn. By rotating or pressing the pressure regulating valve 7, the operating rod of the endoscope is tightly attached to the inner wall of the pressure regulating valve 7. At this time, water is injected and pressurized through the perfusion port 301, and the pressure regulating port 701 can withstand a water pressure above 3 atm without leakage under the condition that the hydraulic dilation balloon 2 is fully expanded and dilated.

Those described above are merely illustrative of specific embodiments of the present disclosure, and are not intended to limit the scope of the present disclosure. Any equivalent variation and modification made by those skilled in the art without departing from the concept and principle of the present disclosure should fall within the protection scope of the present disclosure.

The invention claimed is:

1. A visual pressure regulating catheter, comprising: a catheter body, and a hydraulic dilation balloon and a pressure regulating handle both of which are disposed on the catheter body, an endoscope pressure regulating cavity and a dilation liquid perfusion cavity are formed in the catheter body along an extension direction thereof, the dilation liquid perfusion cavity is communicated with the hydraulic dilation balloon, and the pressure regulating handle is provided with a perfusion port which is communicated with the dilation fluid perfusion cavity and a pressure regulating port which is communicated with the endoscope pressure regulating cavity;

an observation channel is opened at a position on the endoscope pressure regulating cavity within the hydraulic dilation balloon, a camera at a front end of an endoscope sequentially passed through the pressure regulating port, the endoscope pressure regulating cavity and the observation channel and extending into the hydraulic dilation balloon; and an operating rod at a tail end of the endoscope is slidably and sealingly connected to the pressure regulating port and configured to regulate the pressure in the hydraulic dilation balloon when slid axially.

2. The visual pressure regulating catheter according to claim 1, wherein the catheter body has the pressure regulating handle disposed at one end thereof, and a tapered sealing head disposed at the other end thereof, and the hydraulic dilation balloon is disposed close to the sealing head.

3. The visual pressure regulating catheter according to claim 1- or 2, wherein the pressure regulating handle is provided with a pressure regulating valve, and the pressure regulating port is located on the pressure regulating valve.

4. The visual pressure regulating catheter according to claim 1, wherein a side of the observation channel away from the pressure regulating handle is provided with a steering guide piece, and the steering guide piece is provided with an arc-shaped edge inclined to the outside of the endoscope pressure regulating cavity to guide the camera at the front end of the endoscope to extend from the observation channel.

5. The visual pressure regulating catheter according to claim 1, wherein the endoscope pressure regulating cavity is coaxially disposed with the dilation liquid perfusion cavity, and the dilation liquid perfusion cavity is annularly disposed outside the endoscope pressure regulating cavity.

6. The visual pressure regulating catheter according to claim 5, wherein the catheter body comprises an inner catheter body and an outer catheter body are disposed coaxially about the outside of the inner catheter body, so as to form the endoscope pressure regulating cavity in the inner catheter body, and form the dilation liquid perfusion cavity between the inner catheter body and the outer catheter body;

an end of the hydraulic dilation balloon furthest away from the pressure regulating handle is connected to the inner catheter body, an end of the hydraulic dilation balloon closest to the pressure regulating handle is connected to the outer catheter body, and the observation channel sequentially penetrates the inner catheter body and the outer catheter body and is communicated with the interior of the hydraulic dilation balloon.

7. The visual pressure regulating catheter according to claim 1, wherein a central axis of the endoscope pressure regulating cavity is disposed in parallel with a central axis of the dilation liquid perfusion cavity, the endoscope pressure regulating cavity is located at an axial center of the catheter body, a cross-sectional area of the endoscope pressure regulating cavity is larger than that of the dilation liquid perfusion cavity; both ends of the hydraulic dilation balloon are connected to the catheter body, and the observation channel penetrates the catheter body and is communicated with the interior of the hydraulic dilation balloon.

8. The visual pressure regulating catheter according to claim 1, wherein an occlusion balloon is disposed at a position on the catheter body close to the hydraulic dilation balloon, and a dilation liquid perfusion tube is disposed inside the catheter body and communicated with the interior of the occlusion balloon.

9. The visual pressure regulating catheter according to claim 1, wherein at least one developing ring is disposed at a position on the catheter body within the hydraulic dilation balloon.

10. The visual pressure regulating catheter according to claim 1, wherein a guide tube is disposed at an end of the catheter body away from the pressure regulating handle, one end of the guide tube is sealed, and the other end thereof is integrally connected to the catheter body.

11. The visual pressure regulating catheter according to claim 1, wherein the hydraulic dilation balloon is externally provided with a local pressure reinforcing rib, one end of the local pressure reinforcing rib is in sealed connection with the catheter body, and the other end of the local pressure reinforcing rib extends to an end of the catheter body away from the pressure regulating handle and is in sealed connection with the catheter body.

12. The visual pressure regulating catheter according to claim 1, wherein the hydraulic dilation balloon comprises one or more hydraulic dilation balloons disposed continuously along an axial direction of the catheter body, and the one or more hydraulic dilation balloons is made of a transparent material.

13. The visual pressure regulating catheter according to claim 2, wherein the pressure regulating handle is provided with a pressure regulating valve, and the pressure regulating port is located on the pressure regulating valve.

* * * * *